United States Patent [19]

Yanagida et al.

[11] Patent Number: 4,715,944
[45] Date of Patent: Dec. 29, 1987

[54] GAS SENSOR

[75] Inventors: Hiroaki Yanagida, Kashiwa; Tadashi Ogata, Fuchu, both of Japan

[73] Assignee: Kabushiki Kaisha Advance Kaihatsu Kenkyujo, Tokyo, Japan

[21] Appl. No.: 833,400
[22] PCT Filed: May 31, 1985
[86] PCT No.: PCT/JP85/00304
§ 371 Date: Jan. 31, 1986
§ 102(e) Date: Jan. 31, 1986
[87] PCT Pub. No.: WO85/05681
PCT Pub. Date: Dec. 19, 1985

[30] Foreign Application Priority Data

Jun. 1, 1984 [JP] Japan .................. 59-110856

[51] Int. Cl.$^4$ .................................. G01N 27/58
[52] U.S. Cl. .................................. 204/426
[58] Field of Search ............. 204/416, 421, 424, 425, 204/426, 427, 428, 429, 431, 1 K, 1 B, 1 F, 1 N

[56] References Cited

U.S. PATENT DOCUMENTS 4,207,159 6/1980 Kimura et al. .................. 204/426
4,296,148 10/1981 Friese ........................... 427/125
4,462,890 6/1984 Torida et al. .................... 204/425
4,622,105 11/1986 Liu et al. ........................ 204/1 T

FOREIGN PATENT DOCUMENTS 58-214851 12/1983 Japan .

OTHER PUBLICATIONS

M. Gauthier and A. Chamberland, "J. Electrochem. Soc." 124 (1977) 1579.

Primary Examiner—John F. Niebling
Assistant Examiner—Ben C. Hsing
Attorney, Agent, or Firm—Finnegan, Henderson, Farabow, Garrett & Dunner

[57] ABSTRACT

If a part of the surface of a solid electrolyte (1) is covered with a layer (2) of a metal salt capable of forming a dissociative equilibrium with a gas component to be measured and the remaining surface of the solid electrolyte (1) is substantially completely sealed and coated with a gas-intercepting layer (3), there can be provided a gas sensor having a simple structure, the size of which can be drastically reduced, and the operation characteristics of this gas sensor are very stable.

9 Claims, 3 Drawing Figures

GAS SENSOR

TECHNICAL FIELD

The present invention relates to a gas sensor. More particularly, the present invention relates to a structure of a novel solid electrolyte type gas sensor for measuring the concentrations of various gas components such as $CO_2$, $Cl_2$, $SO_x$, and $NO_x$.

BACKGROUND ART

A solid electrolyte is a substance in which an electric current is caused to flow by migration of ions in the solid. If a solid electrolyte cell, in which a gas component to be detected, contained in the gas to be tested, is used as a reactant, is fabricated by using such a solid electrolyte, the concentration of the intended gas component can be known from the amplitude of the electromotive force of the cell or an electric current that can be taken out from the cell. This gas sensor is called "a solid electrolyte type gas sensor".

Various solid electrolyte type gas sensors differing in the structure have been proposed (see Mizusaki, Yamauchi and, Fueki, "Ideas of Solid Electrolyte Sensors", Electrical Chemistry and Industrial Physical Chemistry, Vol. 50, No. 1, pages 7–12, 1982, Yamauchi and Fueki, "Solid Electrolyte Gas Sensors", ibid, pages 46–53, and literature cited therein). In most conventional solid electrolyte type gas sensors, a reference electrode to be contacted with a standard gas should be disposed, and therefore, the structure is complicated and the size is inevitably large. On the other hand, solid electrolyte type gas sensors having a structure in which a standard gas is not necessary are defective in that a satisfactory stability cannot be obtained. Accordingly, only a stabilized zirconia $O_2$ sensor is practically used at the present.

DISCLOSURE OF THE INVENTION

Under this background we made research and, as a result, found that if a part of the surface of a solid electrolyte is covered with a layer of a metal salt capable of forming a dissociative equilibrium with a gas component to be measured and the remaining part of the surface of the solid electrolyte is substantially completely sealed and covered with a gas-intercepting layer so as to prevent contact with the ambient atmosphere as much as possible, there can be obtained a solid electrolyte type gas sensor in which the structure is simplified, the size is drastically reduced, and the operation characteristics are sufficiently stable. We have completed the present invention based on this finding.

More specifically, in accordance with the present invention, there is provided a gas sensor comprising a solid electrolyte, a measurement electrode attached to a part of the surface of the solid electrolyte, a layer of a metal salt capable of forming a dissociative equilibrium with a gas component to be measured, which covers the surface of the measurement electrode and the measurement electrode-surrounding region of the surface of the solid electrolyte, a reference electrode attached to a part of the surface, not covered with the metal salt layer, of the solid electrolyte, a gas-intercepting layer covering the surface of the reference electrode and substantially all of the remaining surface, not covered with the metal salt layer, of the solid electrolyte, and lead lines for taking out potentials from the measurement electrode and the reference electrode.

This gas sensor is prominently characterized in that a standard gas is not necessary and the gas sensor has a sealed structure in which only the metal salt layer falls in contact with the measurement atmosphere such as the gas to be measured, apart from the gas-intercepting layer, and the solid electrolyte is completely isolated from the ambient atmosphere. The gas sensor of the present invention is decisively distinguishable over the conventional techniques in the above-mentioned characteristic feature.

The operation mechanism of the gas sensor of the present invention having the above-mentioned structure has not been completely elucidated, but in view of the fact that, as illustrated in the examples given hereinafter, the gas sensor of the present invention has a sufficient operation stability and the generated electromotive force is in accord with Nernst's equation, it is presumed that a very simple cell system depending only on the dissociative equilibrium of the metal salt may probably be realized stably. Namely, in the conventional gas sensor structures, isolation of a solid electrolyte, which is ordinarily a highly reactive substance, from the ambient gas is not sufficiently taken into account, but the solid electrolyte is positively exposed to the ambient gas, and therefore, it is considered that, due to difficult to control disturbance factors, attainment of stability and reproducibility is difficult.

According to the structure of the gas sensor of the present invention, the concentration of a gas component to be measured can be substantially measured just based on the dissociative equilibrium reaction of the metal salt. Therefore, if the kind of the metal salt or solid electrolyte is appropriately selected, the application range of the gas sensor can be broadened with ease.

A metal salt capable of forming a dissociative equilibrium with a gas component to be measured, such as $CO_2$, $Cl_2$, $SO_x$, or $NO_x$, is used for the metal salt layer of the gas sensor. For example, there can be mentioned $Li_2CO_3$, $Na_2CO_3$, $BaCO_3$, $SrCO_3$, $CaCO_3$, $MgCO_3$, $PbCO_3$, $FeCO_3$, $ZnCO_3$; $NaCl$, $AgCl$, $CaCl_2$, $PbCl_2$, $CdCl_2$, $CuCl_2$, $CoCl_2$, $MnCl_2$, $NiCl_2$, $FeCl_2$, $ZnCl_2$, $BiCl_2$, $MgCl_2$, $VCl_2$; $Na_2CO_4$, $BaSO_4$, $SrSO_4$, $CaSO_4$, $Ag_2SO_4$, $CdSO_4$, $NiSO_4$, $ZnSO_4$, $CoSO_4$; $NaNO_3$, $Ba(NO_3)_2$, $Ca(NO_3)_2$, and $AgNO_3$. The metal salt layer may be formed by coating the metal salt directly on the surface of the solid electrolyte or for example by mixing the metal salt with a ceramic powder and sintering the mixture on the surface of the solid electrolyte. Furthermore, the metal salt may be formed into a film having a thickness of about 1 $\mu$m by sputtering.

As pointed out hereinbefore, selection of an appropriate metal salt can be presupposed to some extent based on Nernst's equation according to the application conditions of the sensor, but, generally, a metal salt having a higher dissociative equilibrium partial pressure is preferred. For example, $Li_2CO_3$ and $Na_2CO_3$ have a high dissociative equilibrium partial pressure and hence, they are preferred.

A conductor for the metal ion of the metal salt used may be used as the solid electrolyte of the gas sensor. For example, as the solid electrolyte having a lithium ion as the electroconductive carrier, there can be mentioned $Li/\beta$-alumina, $Li_{14}(CeO_4)_4$, etc., and as the solid electrolyte having a sodium ion as the electroconductive carrier, there can be mentioned $Na/\beta''$-alumina, $Na/\beta$-alumina, $Na_2Zr_2PSi_2O_{12}$, $Na_3Zr_2Si_2PO_{12}$ (NASI- CON), $Na/\beta$-$Ga_2O_3$, $Na/Fe_2O_3$ etc. Furthermore, as the solid electrolyte having a potassium ion as the electroconductive carrier, there can be mentioned $K/\beta$-alumina and $K_{1.6}Al_{0.8}Ti_{7.2}O_{16}$, and as the solid electrolyte having a calcium ion as the electroconductive carrier, there can be mentioned CaS etc. These solid electrolytes are described in detail in the above-mentioned literature and the references cited therein For example, $Li/\beta$-alumina is expressed as $Li_2O.11Al_2O_3$, $LiO_2$ is intruded in layers of spinel blocks composed of alumina, and $Li^+$ migrates easily in the layers.

There is a relation between the shape of the solid electrolyte and the response time of the gas sensor, so the response time can be shortened by reducing the thickness of the film of the solid electrolyte.

The above-mentioned solid electrolytes can be easily prepared and are commercially available.

The gas-intercepting layer of the gas sensor of the present invention should be substantially gas-impermeable and electrically insulating. Furthermore, the gas-insulating layer should have a heat resistance according to the temperature at which the gas sensor is used. Ceramics, glass, plastics etc. may be used.

For the electrode of the gas sensor, there may be ordinarily used gold, silver, platinum, graphite, $LaCoO_3$ (inclusive of its non-stoichiometrically sintered product), and a ferrite electrode material such as $(K,Na)_2O.67(Fe_{1.97}T_{0.05}O_3)$. When the electrode material is selected, the following factors are taken into consideration. Namely, the diffusion of chemical seeds should be large (the ion conductivity should be large), the electroconductivity should be high, the chemical stability should be high such that the electrode material does not react with the electrolyte, the crystallographic stability should be high such that phase transition is not caused at the temperature at which the gas sensor is used, the vapor pressure should be so low that volatilization is not caused, the metallographic stability should be so high that the electrode material does not react with a conductor line, the mechanical strength should be sufficient, the thermal expansion coefficient of the electrode material should be in accord with that of the electrolyte so that the interface peeling is not caused, and the electrode material should be economically advantageous.

BEST MODE FOR CARRYING OUT THE INVENTION

Figure 1:
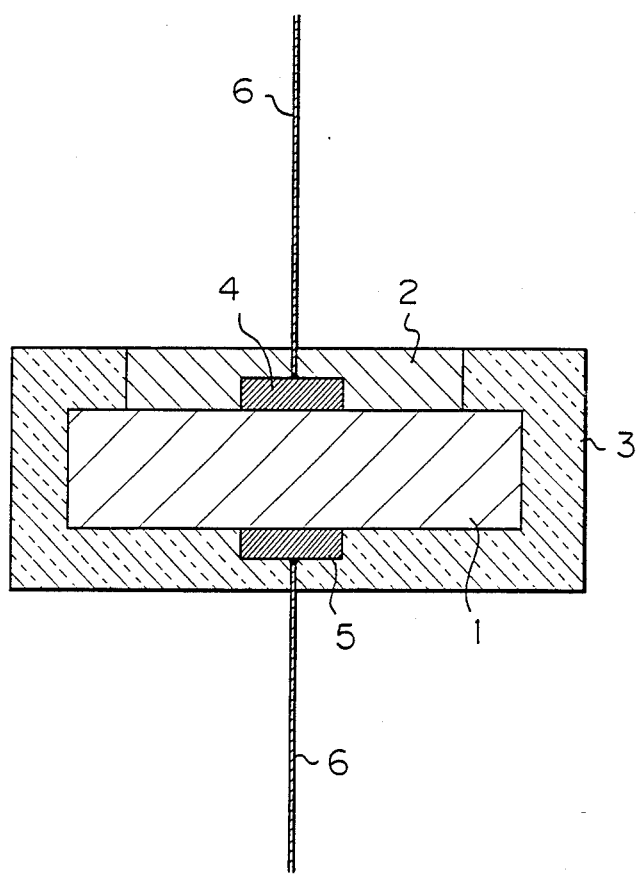
FIG. 1 is a sectional diagram illustrating an example of the structure of the gas sensor of the present invention.

FIG. 1 is a sectional diagram illustrating an example of the structure of the gas sensor of the present invention. A solid electrolyte 1 has, for example, a columnar (disc-like), sheet-like, or filmy shape, typically a columnar (disc-like) shape. A measurement electrode 4 and a reference electrode 5 are attached to two main faces of the solid electrode 1, respectively, and lead lines 6 are connected to the electrodes 4 and 5. A metal salt layer 2 covers a part of the surface of the solid electrolyte 1 inclusive of the surface of the measurement electrode 4. The remaining part, not covered with the metal salt layer 2, of the surface of the solid electrolyte 1 is substantially completely sealed and covered with a gas-intercepting layer 3. Accordingly, in this gas sensor, as pointed out hereinbefore, it is only the metal salt layer 2 that falls in contact with the ambient gas atmosphere to be measured, and the solid electrolyte 1 is completely isolated from the ambient atmosphere.

EXAMPLE 1

A silver paste was spot-coated in the central portions of two main faces of disc-shaped $\beta$-alumina sintered body having a density of about 60%, supplied by Toshiba, $(1.16+x/2)Na_2O.11Al_2O_3.xMgO$; $x \approx 0.8$) having a diameter of 10 mm and a thickness of 3 mm, and the coated silver paste was sintered to form silver electrodes. Simultaneously, silver lines are connected to the silver electrodes, respectively. Then, a mixed paste formed from 0.5 g of $\alpha$-alumina (having an average particle size of 5 $\mu$m) and 2 ml of a saturated aqueous solution of $Na_2CO_3$ (the $Na_2CO_3/Al_2O_3$ molar ratio was 1.2) was coated in a thickness of 1 mm on one main face of the disc-shaped $\beta$-alumina in a region including the silver electrode and having a diameter of about 8 mm, and the remaining surface of the disc-shaped $\beta$-alumina was completely sealed and covered with a heat-resistant inorganic coating agent, "Ceramabond 503" (alumina type inorganic paint supplied by Nissan Kagaku Co.), in a thickness of about 1 mm. The entire assembly was heated and dried (at about 300° C.) by an infrared lamp to obtain a gas sensor having a structure as shown in FIG. 1.

This gas sensor was placed in a furnace maintained at 500° C. under various $CO_2$ partial pressures, and the $CO_2$ partial pressure ($P_{CO2}$) dependency of the generated electromotive force was examined. The obtained results are shown in FIG. 2.

Figure 2:
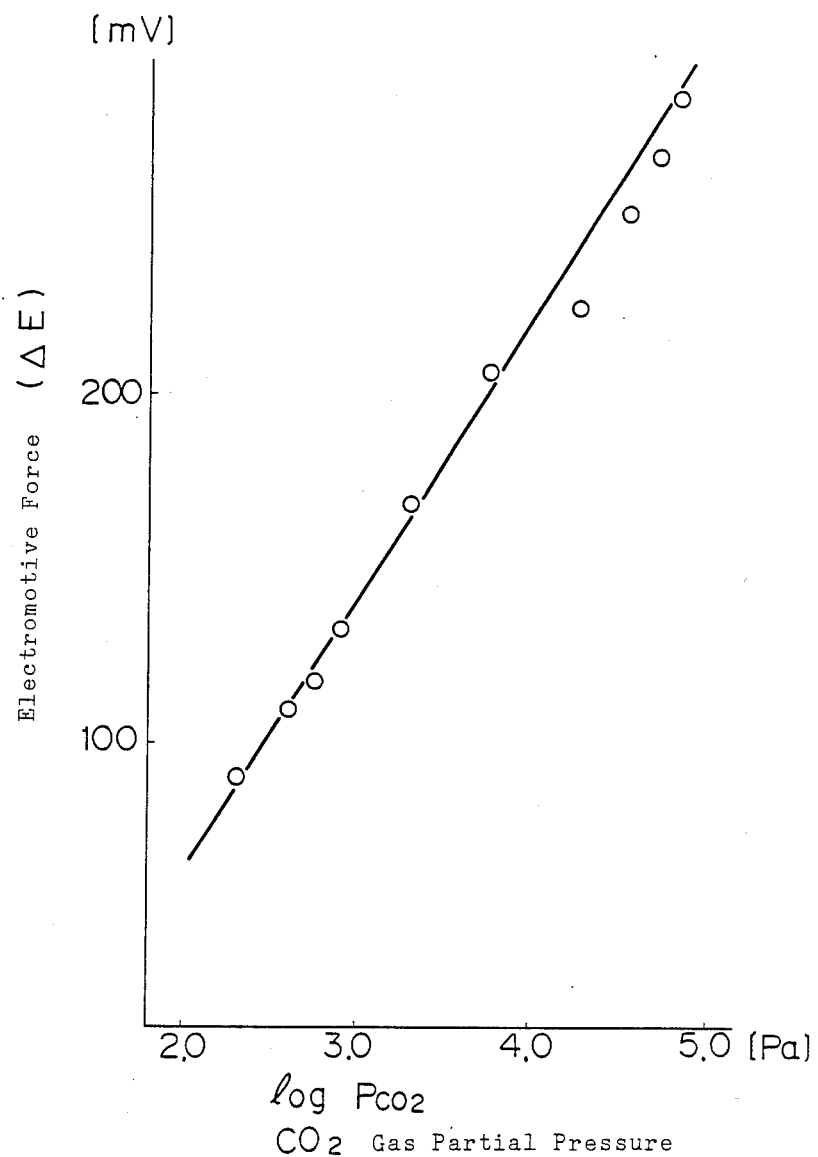
FIG. 2 is a graph showing the $CO_2$ partial pressure dependency of the generated electromotive force of a gas sensor having a structure of $Ag/\beta$-$Al_2O_3/Na_2CO_3$,$Ag(CO_2)$ according to an example of the present invention.

In FIG. 2, the difference $\Delta E$ mV between the electromotive force generated in a standard gas having an $N_2/O_2$ ratio of 4/1 and the electromotive force generated in a gas to be measured, in which a part of $N_2$ is substituted by $CO_2$, is plotted on the ordinate and the $CO_2$ partial pressure $P_a$ is plotted on the abscissa.

As is apparent from FIG. 2, the $CO_2$ partial pressure dependency of the electromotive force had a good linearity in a broad range and was in accord with Nernst's equation. The apparent response speed was very good and the response time was about 10 minutes either when the $CO_2$ partial pressure was increased or when the $CO_2$ partial pressure was decreased. Furthermore, these characteristics were stably maintained even after the lapse of 3 months.

Incidentally, even if the $O_2$ concentration in the standard gas was reduced so that the $O_2$ partial pressure $P_{O2}$ was $10^{-5} P_a$, linearity of the $CO_2$ partial pressure dependency ($P_{CO2}$ dependency) was not lowered.

If the reference electrode side of the disc-shaped $\beta$-alumina was opened, a gas response having reproducibility could not be obtained.

EXAMPLE 2

A gas sensor having a structure as shown in FIG. 1 was fabricated in the same manner as described in Example 1 except that $Li_2CO_3$ was used instead of $Na_2CO_3$, and the $CO_2$ partial pressure dependency of the generated electromotive force was examined in the same manner as described in Example 1.

Figure 3:
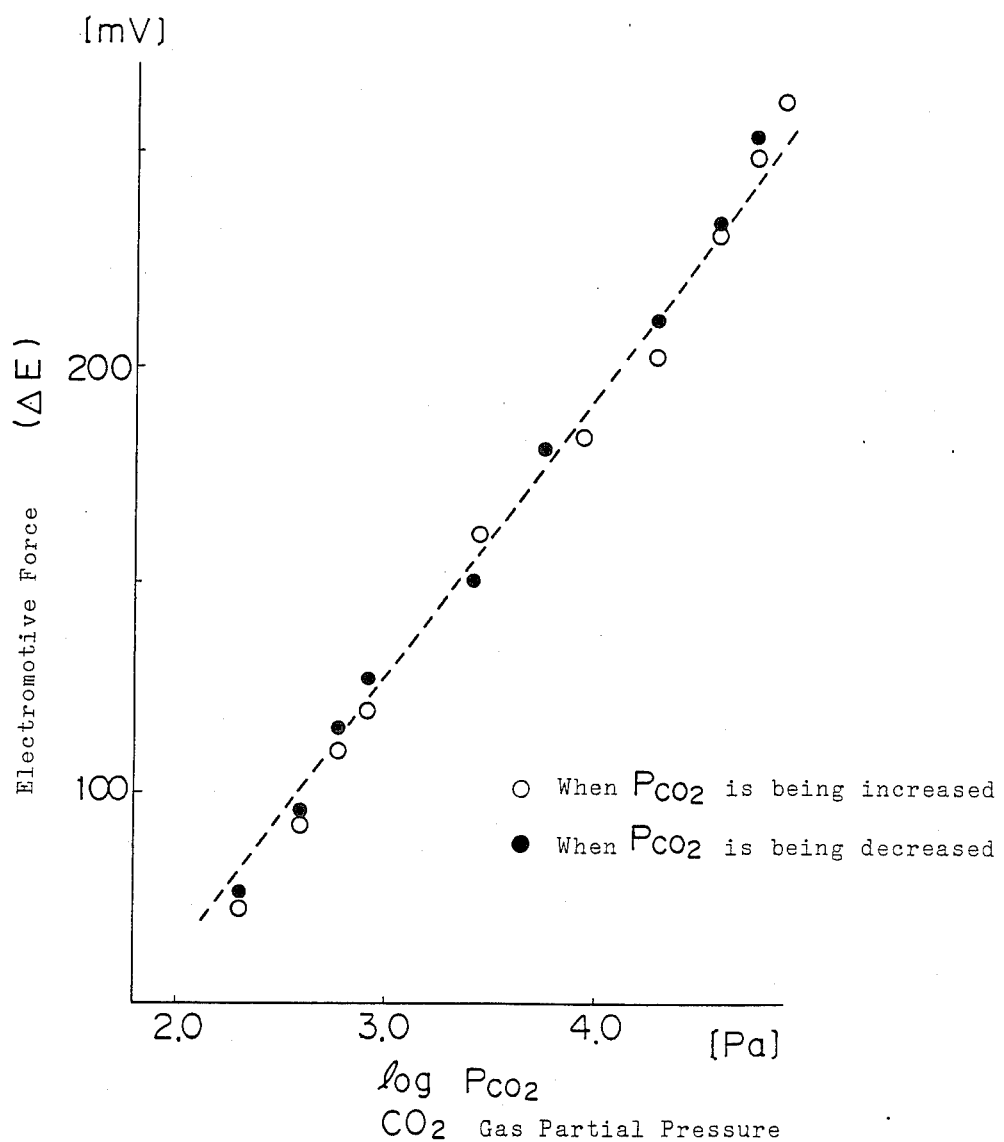
FIG. 3 is a graph showing the $CO_2$ partial pressure dependency of the generated electromotive force of a gas sensor having a structure of $Ag/\beta$-$Al_2O_3/Li_2CO_3$,$Ag(CO_2)$ according to another example of the present invention.

The obtained results are shown in FIG. 3. In FIG. 3, white circles indicate generated electromotive forces measured while the $CO_2$ partial pressure was being increased, and black circles indicate generated electromotive forces measured while the $CO_2$ partial pressure was being decreased.

As is apparent from FIG. 3 this gas sensor also showed a good linearity of the generated electromotive force in a broad range of the $CO_2$ partial pressure. The response speed was very good and the response time was within 5 minutes either when the $CO_2$ partial pressure was increased or when the $CO_2$ partial pressure was decreased. These excellent characteristics were maintained stably for a very long time.

CAPABILITY OR EXPLOITATION IN INDUSTRY

The gas sensor provided according to the present invention has a simple structure, reduced size, and sufficiently stable operation characteristics. For example, this gas sensor can be used for detection of air pollutants in a room, detection of the $CO_2$ concentration in expiration, detection of the $CO_2$ concentration in the exhaust gas of an automobile, and continuous measurement of the $CO_2$ concentration in the fermentation industry.

We claim:

1. A gas sensor for measuring the concentration of $CO_2$, $Cl_2$, $SO_x$ or $NO_x$ in an ambient atmosphere comprising
   (a) a shaped solid electrolyte;
   (b) a measurement electrode attached to a part of the surface of said solid electrolyte;
   (c) a layer of a metal salt capable of forming a dissociative equilibrium with a gas component to be measured and which covers the exposed surfaces of both said measurement electrode and said solid electrolyte adjacent said measurement electrode;
   (d) a reference electrode attached to a part of the surface of said solid electrolyte other than that covered with said metal salt layer;
   (e) a gas-intercepting layer covering the exposed surface of said reference electrode and substantially all of the remaining surface, not covered with said metal salt layer, of said solid electrolyte, said gas intercepting layer being substantially gas impermeable, and sealing said reference electrode from the ambient atmosphere, and
   (f) lead lines for taking out potentials from said measurement electrode and said reference electrode.

2. A gas sensor as set forth in claim 1, wherein the solid electrolyte is composed of Li/$\beta$-alumina, $Li_{14}Zn(CeO_4)_4$, $Li_5AlO_4$; Na/$\beta''$-alumina, Na/$\beta$-alumina, $Na_2Zr_2PSi_2O_{12}$, $Na_3Zr_2Si_2PO_{12}$, Na/$\beta$-$Ga_2O_3$, Na/-$Fe_2O$; K/$\beta$-alumina, $K_{1.6}Al_{0.8}Ti_{7.2}O_{16}$; or CaS.

3. A gas sensor as set forth in claim 1, wherein the metal salt layer is composed of $Li_2CO_3$, $Na_2CO_3$, $BaCO_3$, $SrCO_3$, $CaCO_3$, $MgCO_3$, $PbCO_3$, $FeCO_3$, $ZnCO_3$, NaCl, AgCl, $CaCl_2$, $PbCl_2$, $CdCl_2$, $CuCl_2$, $CoCl_2$, $MnCl_2$, $NiCl_2$, $FeCl_2$, $ZnCl_2$, $BiCl_2$, $MgCl_2$, $VCl_2$; $Na_2CO_4$, $BaSO_4$, $SrSO_4$, $CaSO_4$, $Ag_2SO_4$, $CdSO_4$, $NoSO_4$, $ZnSO_4$, $CoSO_4$, $NaNO_3$, $Ba(NO_3)_2$, $Ca(NO_3)_2$, or $AgNO_3$.

4. A gas sensor as set forth in claim 1, wherein the measurement electrode or the reference electrode or both is composed of silver, gold, platinum, graphite, or a ferrite electrode material.

5. A gas sensor as set forth in claim 1, wherein the gas intercepting layer is composed of ceramics, glass, or plastics.

6. A gas sensor as set forth in claim 1, wherein the solid electrolyte is composed of $\beta$-alumina and the metal salt layer is composed of an alkali metal carbonate.

7. A gas sensor as set forth in claim 6, wherein the alkali metal carbonate is lithium carbonate, sodium carbonate, or potassium carbonate.

8. A gas sensor as set forth in claim 6 or 7, wherein the metal salt layer is composed of an alkali metal carbonate and $\beta$-alumina.

9. A gas sensor as set forth in claim 8, wherein the measurement electrode and the reference electrode are composed of silver.

* * * * *